United States Patent [19]

de Boer et al.

[11] Patent Number: 5,486,368
[45] Date of Patent: Jan. 23, 1996

[54] PRODUCTION OF A CULTURED YEAST PRODUCT FROM WHEY PERMEATE, YEAST CREAM AND YEAST CENTRATE

[75] Inventors: Rudolf de Boer, Wageningen, Netherlands; Roland K. Kramer, Onalaska; Ronald W. McKernan, Whitehall, both of Wis.

[73] Assignee: DMV USA, Inc., La Crosse, Wis.

[21] Appl. No.: 890,513

[22] Filed: May 28, 1992

[51] Int. Cl.$^6$ .............. A23C 21/00; A23L 1/28; C12N 1/16; A23J 1/18
[52] U.S. Cl. .............. 426/41; 426/60; 426/656; 426/657; 435/255.1; 435/255.4; 435/255.7; 435/804
[58] Field of Search .............. 435/41, 804, 255.2, 435/255.4, 255.5, 255.1; 426/60, 455, 647, 655, 657, 41, 656

[56] References Cited

U.S. PATENT DOCUMENTS

| | | | |
|---|---|---|---|
| 3,720,519 | 3/1973 | Hamilton | 426/583 |
| 3,728,128 | 4/1973 | Luksas | 426/41 |
| 3,818,109 | 6/1974 | Bechtle | 435/255 |
| 3,968,257 | 7/1976 | Müller | 426/41 |
| 4,055,666 | 10/1977 | Jeffreys et al. | 426/31 |
| 4,081,367 | 3/1978 | Hulls et al. | 210/610 |
| 4,107,334 | 8/1978 | Jolly | 426/7 |
| 4,165,389 | 8/1979 | du Chaffaut | 426/42 |
| 4,182,777 | 1/1980 | Saunders et al. | 426/62 |
| 4,192,918 | 3/1980 | Stineman et al. | 435/255.21 |
| 4,218,481 | 8/1980 | Chao et al. | 426/60 |
| 4,327,179 | 4/1982 | Moebus et al. | 435/42 |
| 4,426,450 | 1/1984 | Donofrio | 435/243 |
| 4,582,708 | 4/1986 | Tipton et al. | 426/62 |
| 4,810,509 | 3/1989 | Kanegae et al. | 426/60 |
| 5,039,532 | 8/1991 | Jost et al. | 426/41 |
| 5,071,762 | 12/1991 | Shay et al. | 435/247 |

FOREIGN PATENT DOCUMENTS

| | | |
|---|---|---|
| 1170597 | 7/1984 | Canada . |
| 276103 | 2/1990 | German Dem. Rep. . |
| 3007383 | 9/1981 | Germany .............. 426/60 |
| 3742318 | 4/1988 | Germany . |
| 976929 | 11/1982 | U.S.S.R. . |
| WO82/02323 | 7/1982 | WIPO . |

OTHER PUBLICATIONS

Antier, P., et al., 1990, "Influence of Composition of the Culture Medium on the Behaviour of *Kluyveromyces fragilis* in Chemostat Culture", *Proc. Biochem.*, pp. 9–13.

Bayer, K., 1983, "Trace Element Supplementation of Cheese Whey for the Production of Feed Yeast," *J. Dairy Sci.*, vol. 66, pp. 214–220.

Hegenbart, S., 1992, "Flavor Enhancement: Making the Most of What's There," *Food Prod. Des.*, pp. 56–70.

Meyrath, J. and K. Bayer, 1979, Chapter 8, "Biomass from Whey," In: *Economic Microbiology*, vol. 4, A. H. Rose (Ed.), Academic Press, New York, pp. 207–269.

Prendergast, K., 1974, "Protein Hydrolysate–A Review," *Food Trade Review*, pp. 14–21.

Shay, L. K. and Wegner, G. H., 1986, "Nonpolluting Conversion of Whey Permeate to Food Yeast Protein," *J. Dairy Sci.*, vol. 69, pp. 676–683.

*Primary Examiner*—David M. Naff
*Attorney, Agent, or Firm*—DeWitt Ross & Stevens

[57] ABSTRACT

A modified cultured yeast product for human and animal consumption is produced by combining yeast cream and yeast centrate to produce a cream/centrate mixture, autolyzing the mixture, inactivating by heating the mixture and optionally drying. After autolysis, hydrolysis may be carried out by the use of acids, alkalis or enzymes. The yeast cream and yeast centrate are preferably produced by culturing *Kluveromyces marxianus* or *Candida intermedia* in a whey permeate and separating yeast cream and yeast centrate from the cultured whey permeate. The cream and centrate are combined such that the ratio of total solids of cream to total solids of centrate is between about 0.3 and 1.6 and preferably about 1:1.

5 Claims, 1 Drawing Sheet

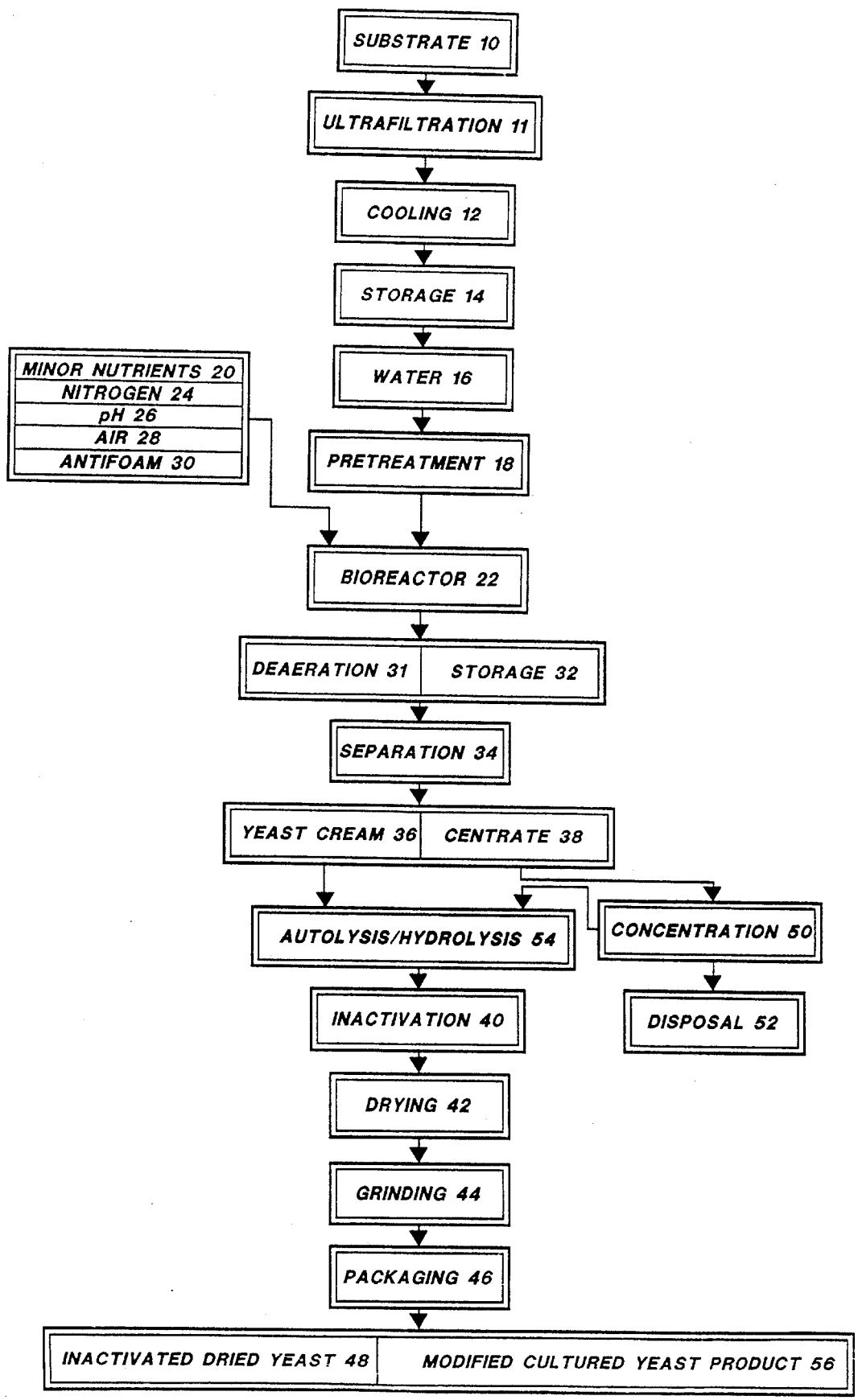

PRODUCTION OF A CULTURED YEAST PRODUCT FROM WHEY PERMEATE, YEAST CREAM AND YEAST CENTRATE

FIELD OF THE INVENTION

The present invention relates to a process for producing yeast products and modified cultured yeast products from lactose-containing substrates. The invention is further directed to reducing or eliminating environmentally-undesirable waste discharge during a yeast production process.

DESCRIPTION OF PRIOR ART

Lactose is the primary milk sugar in milk and milk products. It is used in food supplements and in pharmaceutical preparations. Lactose also provides a nutritional medium for a host of microorganisms, among them yeast. Although lactose can provide a nutritional medium for yeast in the form of whole milk, other lactose-containing substrates, notably whey, can be utilized.

Whey is the residual liquid or by-product after removal of fat and casein from whole milk. The major components in whey are lactose (approximately 75% on a total solids basis), protein (approximately 13%) and ash (approximately 9%). The ratio between the components varies depending on the process involved. Examples of whey by-products include acid or sweet whey, deproteinized whey, whey permeate, deproteinized and partially delactosed whey, and other products which have a reduced lactose content.

Because whey has a low protein content, it is precluded from being accepted as a high-grade food product. Additionally, only a part of the whey can be used for the production of valuable products such as whey powder, whey protein concentrates and lactose. Unfortunately, the quantity of whey produced during a dairy operation usually exceeds any significant demand for the by-product. Further, the market demand for whey products does not justify the expense of either transporting liquid whey from the factory or drying the whey. Thus, a significant amount of the whey or its derivatives must be eliminated.

Because of its high organic content, whey cannot simply be disposed in a waste treatment plant without polluting the environment. Pollution is usually expressed in parts per million Biochemical Oxygen Demand (ppm BOD). The BOD value of whey is on the order of 50,000 ppm, which is much too high to allow whey to be eliminated by normal sewage treatment plants. The liquid is usually field sprayed, which can be an expensive operation. Therefore, effective methods of efficiently utilizing whey are sought.

One method is to utilize the whey or its derivatives as a growth medium for microorganisms in a fermentation process. For example, whey can be used in a fermentation process with lactose-utilizing yeast strains to produce a marketable yeast product. Examples of such processes are found in U.S. Pat. Nos. 3,968,257 to Müller, 4,055,666 to Jeffreys et al., 4,192,918 to Stineman et al., 4,218,481 to Chao et al., 4,327,179 to Moebus et al., 4,426,450 to Donofrio, 4,810,509 to Kanegae et al, 5,039,532 to Jost et al., and in Meyrath, J. and K. Bayer, 1979, Chapter 8, "Biomass from Whey," In: *Economic Microbiology*, vol. 4, A. H. Rose (Ed.), Academic Press, New York, pp. 207–269.

After the yeast product is produced, it is used "as is" for an animal feed supplement or the like, or the yeast cells may be concentrated to a total solids (TS) level between about 10% and 30% (w/v). The term "total solids," as used herein, refers to the amount of material obtained after a representative sample of the product is dried to constant weight. The yeast concentrate, termed "yeast cream," can be utilized as a wet feed additive. It can also be spray or drum-dried into a far more valuable dried inactivated yeast.

The effluent byproduct, termed "yeast centrate" or "centrate," is the non-yeast biomass solid product remaining after separation of the yeast biomass to form the yeast cream. The centrate has heretofore been disposed of as a waste product. Disposing of the centrate is, however, environmentally undesirable due to the remaining BOD and milk minerals. Thus, the centrate should be further processed before it can be disposed.

SUMMARY OF THE INVENTION

The present invention overcomes the above-mentioned disadvantages by providing a process which utilizes the centrate to form an alternative yeast product, termed a "Modified Cultured Yeast Product" or "MCYP." The MCYP can be formed in a specialized MCYP process system, or it can be formed as part of a larger process scheme involving the production of the yeast product produced according to the prior art processes.

The MCYP is the result of a process involving the combination of part of the yeast cream and the yeast centrate. Valuable milk minerals, which are often removed with the centrate, are included in the MCYP. The effluent remaining after the MCYP has been formed has a BOD value which is significantly below the maximum acceptable level for disposal. Thus, the effluent can be conveniently and safely eliminated in a waste treatment sewage plant or in a stream.

The present invention is generally directed to a process for making a MCYP from a lactose-containing substrate, which process includes combining a yeast cream and a yeast centrate in quantities such that the ratio of total solids of the yeast cream to the total solids of the centrate is between approximately 0.3 and 1.6, preferably a ratio of 1:1, and culturing this combination to produce an edible modified yeast product.

The present invention is particularly directed to a process for producing a yeast product and a MCYP utilizing a lactose-containing substrate such as whey permeate as the growth medium for a lactose-utilizing yeast. The whey permeate is heat-treated to destroy bacteria and to avoid undesirable breakdown of lactose. The heat-treated whey permeate is preferably inoculated with a yeast culture in a bioreactor and maintained under yeast growth conditions until a substantial quantity of yeast is produced in the whey permeate. The yeast-rich bioreactor content is withdrawn from the bioreactor and separated into a yeast cream and an effluent centrate. The yeast cream is then divided into a first portion and a second portion. A dried, inactivated yeast is recovered from the first portion of the yeast cream. The centrate is concentrated and combined with the second portion of the yeast cream and subsequently autolyzed, or autolyzed and hydrolyzed. The autolysate, which has flavor enhancement properties, is heat inactivated and further processed to recover a MCYP.

The present invention is further directed to a process for preparing a MCYP using partially delactosed whey permeate as a growth medium. The partially delactosed whey permeate is heat-treated and inoculated with a yeast culture in a bioreactor and maintained in the bioreactor under yeast growth conditions until a substantial quantity of yeast is produced in the whey product. The yeast-rich liquid is withdrawn from the bioreactor and subjected to separation conditions in order to separate a yeast-rich cream from an effluent centrate. The centrate is then concentrated and combined with the yeast cream and autolyzed. The yeast-rich liquid can also be concentrated directly by evaporation if the temperature is kept below 130° F. (54° C.). The autolysate is then heat-treated and further processed to produce a MCYP.

The present invention is also directed to a MCYP, comprising in combination a yeast cream and a yeast centrate, each having a total solids content between about 5% and 40% (w/v), wherein the ratio of the total solids content between the yeast cream and the yeast centrate is between approximately 0.3 and 1.6, and the centrate has a BOD below about 100 ppm. The MCYP can be used as a food supplement.

Because the present invention contemplates the further use of the waste-whey product, the problem of whey disposal is reduced such that the effluent is free of salts and has an extremely low BOD value, i.e., less than about 100 ppm, and preferably less than 50 ppm. This approach to whey disposal is very attractive environmentally.

Aside from assisting in reducing environmental waste problems, the process of the present invention advantageously creates two highly usable products: (1) a substantially pure yeast protein product, i.e., dried inactivated yeast; and (2) MCYP, i.e., a combination of the yeast cream and the centrate, which produces unexpected and more desirable flavors for use in food for human consumption and feeds for animal consumption due to autolyzing and hydrolyzing this mixture. Therefore, a significant portion of a waste product, i.e., the whey by-product of cheese factories or the like, can be converted into usable feed and food products and at the same time eliminate environmentally objectionable waste products having high salt content and BOD values.

Yeast products described in this invention can be further combined with other ingredients, e.g., molasses, grilled flavors, smoked flavors, and meat flavors, to produce flavor combinations that can be used in value-added flavor enhancer applications such as savory soups; seasoning blends; sauces and gravies; and cheese and dairy formulations.

Other objects and advantages of the present invention will be apparent from the following detailed description of the invention, the figure and the examples.

DESCRIPTION OF THE DRAWING

The Figure is a schematic drawing illustrating the steps used for the production of an inactivated dried yeast product and a MCYP.

DETAILED DESCRIPTION OF THE INVENTION

The present invention is specifically directed to a process for preparing dried inactivated yeast along with MCYP. The process for preparing the MCYP requires the following starting products in defined proportions: a yeast cream and a yeast centrate.

The term "yeast cream" defines a yeast product having a total solids (TS) level between about 10 and 30% weight per volume (w/v). The yeast cream may be produced from yeast strains of the Kluyveromyces, Candida and Torulopsis families. Preferably, the family Kluyveromyces is used for food-grade yeast, and the family Candida is used for feed-grade yeast. Reference is made to the section on the yeast families further in the specification for details of the yeast strains.

Although the yeast cream is usually prepared in a bioreactor as described later in the specification, yeast creams having the above-mentioned characteristics can be obtained in other ways. Yeast creams are also commercially available.

The term "concentrated centrate," as used herein, refers to a fluid having between 5% and 40% TS (w/v), preferably about 15% TS (w/v) and is low in nitrogen. It is predominantly a milk product and includes minerals, which assist in the production of the MCYP. Preferably, less than 5% (w/v) of the total yeast biomass is found in the centrate. Like the yeast cream, the concentrated centrate may be obtained commercially. However, a readily available source is from a yeast bioreactor as described hereinafter.

The process for preparing the MCYP includes combining the yeast cream and the centrate, after concentration according to technologies known to the art, in quantities such that the ratio of total solids between the yeast cream and the centrate solids is between approximately 0.3 and 1.6 and preferably about 1:1. Although the 1:1 ratio of total solids between the yeast cream and the centrate may deviate, deviations such that the ratio is less than 1:1 can result in undesirable consequences in the drying phase and in the ultimate flavor and color of the MCYP.

At some point before or after the concentrated centrate is added to the yeast cream, the yeast cells are autolyzed, i.e., self-lysed, and/or hydrolyzed, i.e., treated by external enzymes. By autolyzing this mixture, all of the yeast centrate can be utilized.

Autolysis

Autolysis involves the breakdown of the cellular constituents as a result of the action of enzymes contained within the cells. Autolysis is the self-lysis of yeast cells and is known to the art. The temperatures normally applied are between 104° F. (40° C.) and 140° F. (60° C.) for a 20 to 40 hour period. The self-lysis process can be accelerated by the use of sodium chloride, although the finished product will have a higher sodium content.

Centrate, added before autolysis to the yeast cream, has a positive effect on the autolysis process and results in a favorable flavor. The batch autolysis process results in a MCYP with flavor enhancement properties, which are useful for pet food as well as for human consumption. The finished products have a low free glutamate content (approximately 1%) and a sodium content between 1.5% and 3.0% and are particularly suitable for food applications.

Hydrolysis

Hydrolysis is the catalytic breakdown of the cellular constituents. Hydrolysis is generally utilized to speed the process. Hydrolysis may be accomplished by the use of acids (acid hydrolysis), alkalis (alkaline hydrolysis) or enzymes (enzyme hydrolysis).

Acid hydrolysis is used for the solubilization of yeast. Strong acids such as hydrochloric acid will degrade macromolecules, e.g., proteins, carbohydrates and nucleic acids to subunits of higher solubility.

Enzyme hydrolysis is generally associated with the proteolytic breakdown of protein substrates such as fish waste, fish, meat, whey protein, casein and gelatin. In the case of *Kluyveromyces marxianus* (*K. marxianus*) external proteolytic enzymes such as pancreatin and papain are used to support the autolysis, which results in shorter process times and more pronounced flavor. Hydrolysis reactions are generally carried out over a temperature and pH range of 120° F.–140° F. (49° C.–60° C.) and 4.0 to 6.0, respectively. Hydrolysis reaction times usually range between 2 and 8 hours.

The mixture of the present invention is preferably subjected to enzymatic hydrolysis in a known manner using mixed or purified proteolytic enzymes. Examples of proteolytic enzymes include trypsin, chymotrypsin, papain and pancreatin. The preferred external enzymes are pancreatin and papain. Papain is derived from the papaya plant, and pancreatin is derived from the pancreas of the pig. Pancreatin contains not only a protease, but also lipases and amylases. The contemplated process is a batch autolysis/hydrolysis with the temperature and pH adjusted.

Heat-Treatment

The heat-treatment process is conducted to inactivate the dried yeast products and MCYP. The conditions include a temperature range between about 160° F. (71° C.) and 185° F. (85° C.) for a period of time between about 20 seconds and 10 minutes. For the MCYP, more severe conditions are desirable, e.g., 180° F. (82° C.) for 10 minutes, while for inactivated dried yeast product milder conditions, e.g., 175° F. (79° C.) for 5 minutes, are useful to destroy yeast cells and any possible microbiological contamination.

Drying

The yeast products can be easily drum dried according to processes well known to the art. An acceptable light brown powder can be obtained if the ratio of cream solids to concentrated centrate solids is between 0.3 and 1.6. This is equal to 10% to 60% of the total amount of yeast cream separated, respectively. Furthermore, the residual carbohydrate should be kept at no more than 0.5 g/l during fermentation to avoid browning during drum drying. The process conditions should be considered in addition to the carbohydrate content of the bioreactor products. High temperature and long-residence time on the drum dryer should be avoided to restrict browning and to reduce caramel formation. If these circumstances are kept under control, the product of drum drying has a "roasted flavor" which is described as pleasing to the taste. Because of the generally higher product temperature during drum drying, some additional volatiles may be lost. In this respect, drum drying has an advantage over spray drying. However, at a high residual carbohydrate level, an unacceptable burned taste is formed. Both yeast products are then ground by a hammer mill and sifted, also known to the art, and packaged.

The MCYP has an attractive flavor and therefore can be used as a flavoring agent in pet food and other types of food. The flavor of the MCYP is closely related to the nutrients used. High sulfur levels (sulfate) are responsible for a chemical off-flavor, while the combination of phosphoric acid and hydrochloric acid causes a more pleasant taste in addition to the existing salty flavor. Products with a low pH have a somewhat pleasant acid taste.

Process for Preparing MCYP and Yeast Product

As described earlier, the process for preparing the MCYP can be combined with known processes for preparing a yeast product. The process will now be described in detail with reference to the Figure.

Lactose-Containing Substrate 10

Any liquid dairy by-product, which contains lactose, can be used as the starting component for the process of the present invention. Likewise, hydrolyzed lactose (glucose and galactose) can be used as a substrate for the growth of numerous species. The use of hydrolyzed lactose offers broader capabilities to the process of the present invention. For example, a broader range of yeast species, such as Bakers Yeast which belongs to the Saccharomyces family and which preferentially uses glucose, can be incorporated into the process of the present invention. For purposes of the present invention, the starting component is termed "lactose-containing substrate," and is referenced in the Figure by the number 10. Lactose by-products often result from the manufacture of casein, cheese and cheese products. However, it is within the scope of the present invention to manufacture a substrate which contains the appropriate components.

The present invention is specifically directed to a process utilizing a whey permeate. Examples of the whey permeate are listed above. The process of the present invention utilizes the useful components in the whey permeate as a growth medium for yeast. Compared to whey permeate, whey is a less preferable lactose-containing substrate.

If a dairy by-product is used as the substrate 10, a significant amount of protein must be removed before the substrate 10 can be used in the present process. Preferably, the substrate 10 is deproteinized. As used in this context, the term "deproteinized" means that a sufficient amount of protein has been removed from the substrate 10 such that the end products, i.e., the yeast cream and the centrate, are substantially void of proteins from the substrate 10. Additionally, a substantial amount of the fat in the product is preferably removed from the substrate 10. Both the protein and fat component may interfere with the fermentation process.

Ultrafiltration 11

The whey substrate can be used efficiently only if the required nutrients are provided and the culture conditions are carefully controlled. The whey substrate is clarified through an ultrafiltration process 11, well known in the art in order to remove the valuable proteins which can be processed into whey protein concentrates. An example of an ultrafiltration process, which may be applied to the present invention, is described in U.S. Pat. No. 3,968,257 to Müller. The remaining whey permeate has a general composition as follows (w/v): 5% TS, 85% lactose/TS, 10% ash/TS, and 4% non-protein nitrogen (NPN/TS). The whey permeate has a BOD value of approximately 50,000 ppm, far exceeding the safe content for subjecting this liquid to a waste-water treatment process.

Cooling 12 and Storage 14

The whey permeate from the ultrafiltration process is cooled at step 12 to a temperature below 45° F. (7° C.) and stored in a storage facility 14 until required for use.

Prior to the heat pretreatment step, the lactose content of the whey permeate may be standardized with potable water at step 16 depending on the aeration system and the yeast species involved. p Pretreatment 18

Before the whey permeate is fed into the bioreactor 22, it is heated to a temperature between approximately 162°–185° F. (72°–85° C.), preferably 162° F. (72° C.) for approximately 20 seconds at the pretreatment step 18.

Minor nutrients 20, such as trace minerals and vitamins, are added to the whey permeate prior to entering the bioreactor 22 to control an efficient conversion of lactose into yeast biomass. The types of nutrients, which are added to the ultrafiltered whey permeate, depend on the yeast species. In the case of the yeast *Candida intermedia* (*C. intermedia*), the following trace element composition of Bayer, K. (*J. Dairy Sci.*, 1983, vol. 66, pp. 214–220) is suitable(g/l): 0.3, $CuSO_4 \cdot 5H_2O$; 0.8, $MnSO_4 \cdot H_2O$; 0.4, $Na_2MoO_4 \cdot 2H_2O$; 3.0, $ZnSO_4 \cdot H_2O$; 4.0, $FeClF_3 \cdot 6H_2O$. The following trace elements and vitamins described by Antier, P. et al. (*Proc. Biochem.*, Feb. 1990, pp. 9–13) are suitable for the growth of the yeast *K. marxianus* (g/l): 0.4, $H_3BO_3$; 0.032, $CuSo_4 \cdot 5H_2O$; 0.08, Kl; 0.32, $MnSO_4 \cdot H_2O$; 0.16, $Na_2MoO_4$; 0.32, $ZnSO_4$; 0.64, $FeCl_3 \cdot 6H_2O$; 0.8, Calcium pantothenate; 0.8, thiamine; 0.8, m-inositol; 0.8, pyridoxine; 1.0, nicotinic acid; and 0.008, biotin.

Bioreactor 22

The substrate 10 then enters the fermentation zone or bioreactor 22. In the bioreactor 22, the component structure of the substrate is further altered to satisfy yeast growth conditions.

Fermentation may be either continuous, semi-continuous or batch-type. For convenience and economy, a continuous fermentation technique is preferred. Suitable fermentation reactors are known to the art. Reference is made to *Meyrath and Bayer* (supra.) for examples of suitable fermenters. Under this procedure, the heat-treated whey permeate is continuously introduced into the bioreactor 22, and the yeast biomass product from the bioreactor 22 is harvested to storage tanks 32 where they are held under temperature-controlled conditions for a suitable period of time.

The fermentation conditions include temperatures in the range of about 77° F. (25° C.) to 122° F. (50° C.). The temperature depends in some part on the species of yeast used in the bioreactor. Retention times between about 2 and 8 hours are desirable for culture stability. *C. intermedia* was adapted to grow in a continuous bioreactor operation over a substantial period of time using the following culture conditions: culture temperature of about 82° F. (27.8° C.); a minimum retention time of 2.5 hours; pH 3.8; and oxygen limitation (below 0.5 ppm).

Nitrogen Source 24

Because the whey permeate does not contain enough nitrogen to grow yeast products, a nitrogen source 24 must be added to the fermentation medium. While urea may be used as the nitrogen source, ammonium sulfate combined with diammonium phosphate and sodium hydroxide can also be used. However, aqua ammonia combined with hydrochloric acid or phosphoric acid is preferred as it has been found to be more easily assimilated by yeast.

pH 26

The pH of the bioreactor content can be set between 3.0 and 4.5, preferably 3.8, as a compromise between culture stability and usage of acid. Where aqua ammonia is used as the nitrogen source, the pH of the fermentation medium can be controlled at 26 by adding a constant quantity of aqua ammonium to the medium in an amount which is required to satisfy the nitrogen requirement of the yeast. An acid, such as sulfuric acid, may then be used to adjust the pH of the bioreactor conditions. Alternatively and preferably, the pH may be altered by the combination of a constant supply of phosphoric acid in the medium followed by measured quantities of hydrochloric acid in response to variations in the pH. The use of phosphoric acid and hydrochloric acid reduces the sulfate levels in the end product.

The pH of the whey permeate is adjusted in part to accommodate the yeast in the bioreactor 22 and in part to affect the resulting product. For example, if sulfate is added, the product has a chemical off-flavor.

Air 28

The production of yeast biomass normally requires aerobic conditions. The quantity of air, to the amount of oxygen per unit of yeast biomass, depends on the species and is normally between 0.8 g to 1.2 g oxygen/g yeast. The air 28 can be supplied by various systems such as sparger or jet systems. Air filtration of the incoming air is required to avoid undesirable microbiological contamination.

Anti-Foam 30

Because of the added air 28, control of foaming in the bioreactor is necessary. For this purpose, known food-grade anti-foaming agents 30 are used. The anti-foaming agent is compatible with the use of a membrane unit in downstream processing.

Yeast

The types of yeast, which are most efficient for rapid utilization of lactose, are strains of the Kluyveromyces and Candida families. Examples of suitable Kluyveromyces strains include *K. marxianus, K. aestuarii, K. bulgaricus, K. circerisporus, K. lactis* and *K. wickerhamii*. The most common dairy yeast is *K. marxianus*. This yeast strain is also known as *K. fragilis* or *Saccharomyces fragilis* (*S. fragilis*). An example of the Candida strain is *C. intermedia*. Other yeasts that utilize lactose include strains such as *Torulopsis cremoris* (*T. cremoris*) and *T. spherica*.

A yeast culture is initially inoculated in the bioreactor 22 after the whey permeate is added. The bioreactor 22 then preferably operates under a continuous process. Ideally, yeast is produced in a dynamic equilibrium reaction. In other words, the flow of substrate into the bioreactor 22 is balanced to the flow of yeast biomass out of the reactor. Following fermentation in the bioreactor 22, the yeast product is deaerated 31 and stored 32 in a manner known to the art until further required.

Separation 34

The yeast biomass product from the bioreactor 22 must be concentrated in order to obtain a marketable product. The separation can be carried out by means of various types of equipment known to the art, e.g., microfiltration, vacuum filter, decanter, disc centrifuge, etc. Preferably, the separator 34 is a disc centrifuge unit having a separation efficiency of approximately 95%. The product is separated into a yeast-rich cream (yeast cream 36) and a centrate 38. Preferably, a higher separation efficiency of about 95% is required for the yeast cream 36, since a low-efficiency separation generally has a negative influence on downstream processing. A high percentage of yeast cells in the centrate 38 would make normal evaporation impractical due an inconsistency with the requirements for the MCYP autolysis process (approximate temperature 120° F./49° C.). Equipment with lower efficiencies (e.g., 60%) can be applied if the evaporation step is carried out at temperatures less than 130° F. (54° C.).

Yeast Cream 36

The yeast cream 36 can then be dried and packaged, according to processes known to the art to form an inactivated substantially pure yeast 48. The yeast 48 is preferably inactivated at step 40. To accomplish this, a heat-treatment step should be introduced just before the drying step 42. The heat-treatment step can dramatically reduce the number of viable yeast cells to less than 1 colony forming unit (CFU) per gram and additionally improve the digestibility.

The dried yeast product is then ground at step 44 and packaged at step 46 as described above to form the final inactivated dried yeast 48. The main constituents of the final yeast 48 are on the average 34–47% protein, 6.6–12.2% ash, 4.1–8.0% fat, and 1.1–6.0% moisture. The preferred product is a substantially pure yeast having about 45% protein, 5% moisture, 9% ash, 6% fat and the remaining portion carbohydrate. The yeast can be used for human or animal consumption.

Centrate 38

The centrate 38 is the effluent fluid that is separated from the yeast cream. The centrate 38 includes products which were left after fermentation in the bioreactor 22, products such as ethanol and some acids. As described previously, the centrate 38 contains less than 5% of the total yeast cells; is high in ash content; is low in nitrogen content; and comprises about 1% solids. Further, some of the nutrients which were added for the growth of the yeast remain in the centrate.

Because its TS level is low, the centrate is concentrated at step 50 to a TS level between about 5% and 40% (w/v). Two technologies can be utilized for concentrating the centrate: evaporation and reverse osmosis (RO).

Evaporation is advantageous in that the centrate can be concentrated easily to approximately 30% TS, while the BOD value of the condensate, i.e., the effluent remaining after the centrate is condensed, is extremely low. In most cases, the condensate can be directly discharged into streams.

Reverse osmosis is particularly economical at low TS percentages, i.e., effluents having a TS content of 1–2%. However, the concentration rate is limited due to the osmotic pressure of the feed and fouling of the membranes while the BOD value of the condensate is less than 100 ppm. The latter requires some additional treatment before it can be disposed (52), i.e., discharged into streams.

The concentrated centrate is then combined with the yeast cream 36 and subjected to autolysis and/or hydrolysis steps 54, as described previously. Subsequently it is processed through the inactivation 40, drying 42, grinding 44, and packaging 46 steps, according to the previously described process, to form the MCYP.

The MCYP can be used as a food (for human consumption) or feed (for non-human or animal consumption) supplement. For purposes of the present application the term "food" or "food supplement" includes animal feed and feed supplements.

The food supplement is designed to be added to a standard maintenance ration. The term "standard maintenance ration" includes food or food products well known to the industry for a particular animal. For example, the food supplement of the present application can be added to off-the-shelf pet foods for supplementing pet diets.

The product can be blended or mixed into the ration or sprayed on the ration. The amount of food supplement fed to an animal will vary depending upon the type of animal, the general health and age of the animal, and the sex of the animal. For example, pet food such as dog and cat food can be preferably supplemented with the food supplement of the present invention in amounts ranging from about 1% to 10% (w/v), preferably 1% to 3% (w/v).

The food supplement is prepared according to the previously described process for preparing the modified cultured whey product. The process can be altered depending upon the preference of the consumer. For example, dogs prefer an autolyzed product having a pH of about 5.4. Cats prefer an autolyzed product having a pH of about 4.5. Reference is made to Example 9, infra., for further disclosure of the food supplement.

EXAMPLES

The invention is illustrated by the following examples in which parts and percentages are by weight unless otherwise indicated.

In these examples, except where expressed otherwise, aqua ammonia combined with hydrochloric acid or phosphoric acid was added as a nutrient source primarily because this nitrogen substance is easily assimilated by yeast and the acids have a positive effect on MCYP taste.

For Examples 1–9, the experiments using *C. intermedia* were conducted under the following culture conditions: pH 3.8, temperature 82° F. (28° C.), a retention time of 6 hours, and with oxygen limitation. The dissolved oxygen (DO) level is a tool to influence culture stability. The efficiency of DO to control the feed conversion is limited, as small variations in DO level (0.4–0.6 ppm) can result in a broad range of conversions (42–49%).

Experiments involving *K. marxianus* (Examples 10–17) were conducted under the following conditions: pH 3.8, temperature 108° F. (42° C.), a retention time of 6 hours without oxygen limitation.

The substantially pure yeast product, which was manufactured in these examples, had an average composition as follows: average protein 41% (34–47%), 10% ash (6.6–12.2%), 6% fat (4.1–8.0%) and 4% moisture (1.1–6%).

The MCYP samples were organoleptically tested according to standard procedures in the industry, consisting of tasting and smelling of a 2% solution at approximately 120° F. (49° C.).

Examples 1–5

Examples 1–5 were designed to illustrate the process of the present invention utilizing *C. intermedia*. Whey permeate was processed through an ultrafiltration unit (spiral-wound type), cooled below 45° F. (7.2° C.) and standardized with potable water to 3.8% TS at a rate of approximately 1,600 gal/hr.

The permeate was then heat-treated at 162° F. (72° C.) for 20 sec to reduce the bacterial count and to avoid undesirable breakdown of lactose.

Following heat treatment, the permeate was fed continuously to a bioreactor in which a culture of *C. intermedia* was growing under the following conditions: temperature 82° F. (28° C.), pH 3.8, a retention time of 6 hr and oxygen limited conditions (dissolved oxygen below 0.5). Aqua ammonia (30%) and phosphoric acid (75%) were fed to the bioreactor continuously at a rate of 8.5 gal/hr and 3 gal/hr, respectively. The pH of the bioreactor content was adjusted to 3.8 by the addition hydrochloric acid (31.5%).

By a jet-system, filtered air (2000 SCFM) was blown into the liquid at the bottom of the bioreactor. Foaming in the bioreactor was controlled by using a variable amount of anti-foaming agent (Struktol-JA 673, Stow, Ohio).

After deaeration, the yeast cells were separated by a disc centrifuge at an efficiency not less than 95%. A portion (approximately 100 gal. of the recovered 160 gal) of the yeast cream (17% TS) was inactivated by heat treatment in a scraped surface heat exchanger at a temperature of 172° F. (78° C.) for 20 sec., subsequently followed by a drum-drying step (50 psi) and milling/sifting. The inactivated dried substantially pure yeast (150 lb/hr, 5% moisture) was then packed for shipping.

The centrate from the disc centrifuge, which has a BOD value of about 1500 ppm, was pasteurized at 162° F. (72° C.) for 20 sec and further concentrated to 17% TS in a 3-stage falling film evaporator. The concentrated centrate (60 gal/hr) was combined with the remaining yeast cream (60 gal/hr) and processed through the steps of inactivation, drum drying and milling/sifting. The final MCYP contained about 5% moisture (180 lb/hr) and had a slight brown color. The following table illustrates the results of each of the Examples. Process conditions are also listed.

Examples 1-3

Non-Autolysis and Autolysis of the Yeast *Candida intermedia* under Various Circumstances Followed by Drum Drying

| Examples | 1 | 2 | 3 |
|---|---|---|---|
| Batch No. | T30 | T31 | T32 |
| Conditions | mixture[1] | mixture[1] | mixture[2] |
|  | pH 4.5 | pH 6 | pH 4.5 |
|  | fresh | fresh | 21 h |
|  |  |  | 122° F. |
| Protein breakdown |  |  |  |
| NPN/TN (%) | 40 | 40 | 56 |
| Free glutamic acid (%) | — | 0.3 | 0.5 |
| Taste (2% sol.) | sour bitter | sour flat | sour bouillon |
| Color[3] | + | ++ | ++ |
| Res. Carboh. (g/l) | 0.4 | 0.4 | 0.4 |
| Composition |  |  |  |
| protein | 38 | 35 | 37 |
| fat | 4 | 5 | 5 |
| ash | 26 | 30 | 23 |
| Ash composition |  |  |  |
| phosphorus | 5.2 | 6.2 | 4.7 |
| chloride | 5.5 | 7.1 | 5.8 |
| sulfur | 0.2 | 0.2 | 0.1 |
| potassium | 3.4 | 3.5 | 3.4 |
| sodium | 1.5 | 2.9 | 1.4 |
| calcium | 0.5 | 0.8 | 0.6 |
| magnesium | 0.2 | 0.2 | 0.2 |
| pH (10% sol.) | 4.6 | 5.4 | 4.6 |

[1]non-autolysis conditions
[2]autolysis conditions
[3]+ = tan; ++ = light brown

Examples 4-5

Autolysis/Hydrolysis of the Yeast *Candida intermedia* under Various Circumstances Followed by Drum Drying

| Examples | 4 | 5 |
|---|---|---|
| Batch No. | T33 | T34 |
| Conditions | mixture[1] | mixture[2] |
|  | pH 4.5 | pH 6 |
|  | 21 h | 4 h |
|  | 122° F. | 122° F. |
|  | after A pH 6 | H (0.5%)[3] |
| Protein breakdown |  |  |
| NPN/TN (%) | 56 | 60 |
| Free glutamic acid (%) | 0.3 | 0.7 |
| Taste (2% sol.) | bouillon | toasty bouillon |
| Color[4] | +++ | ++++ |
| Res. Carboh. (g/l) | 0.4 | 0.35 |
| Composition |  |  |
| protein | 35 | 33 |
| fat | 4 | 4 |
| ash | 26 | 23 |
| Ash composition |  |  |
| phosphorus | 5.4 | 4.7 |
| chloride | 6.4 | 5.7 |
| sulfur | 0.1 | 0.2 |
| potassium | 3.8 | 3.7 |
| sodium | 2.7 | 2.3 |
| calcium | 0.7 | 0.6 |
| magnesium | 0.2 | 0.2 |
| pH (10% sol.) | 5.4 | 6.0 |

[1]autolysis (A) conditions
[2]hydrolysis (H) conditions
[3]hydrolysis with 0.5% pancreatin; enzyme dosage calculated on yeast cream solids
[4]+++ = brown; ++++ = dark brown

Example 6

Example 6 was designed to compare spray drying and drum drying and to show the effect of residual carbohydrates on drying. Following the procedure of Examples 1–5, the quantity of yeast cream used for the manufacture of the MCYP was varied. All samples were derived from a bioreactor run in which the residual carbohydrates were kept at a level of approximately 0.4 grams/liter (g/l). The concentrated centrate (60 gal.) was subsequently combined with 80 gal, 60 gal, 40 gal and 16 gal of yeast cream. The ratio of cream solids to centrate solids was 1.3, 1.0, 0.7 and 0.3, respectively. The pH of the mixtures were corrected to approximately 5.

Some of the samples were spray dried (box drier), inlet temperature 385° F. (195° C.), outlet temperature 220° F. (105° C.). Due to a high percentage of milk salts (40% ash/TS) in the mixture with 16 gal of yeast cream, the resulting MCYP had an extremely salty taste. Drum drying became more and more difficult as the quantity of milk salts increased in the yeast cream and concentrated centrate mixture due to the sticky behavior of the added milk salts.

Both the quantity of yeast cream and the level of residual carbohydrates influenced the drum drying results. Four different bioreactor runs were made with 2.3, 1.7, 0.3 and 0.2 g/l residual carbohydrates, respectively. All mixtures of 60 gal concentrated centrate and 60 gal yeast cream were adjusted by a sodium hydroxide solution to pH 6. The MCYP derived from the runs with 2.3 and 1.7 g/l residual carbohydrates had a dark brown color and a burned taste, while the products coming from the bioreactor runs with a low residual carbohydrate level (0.3 and 0.2 g/l) had a light brown color and a pleasant roasted flavor.

Example 7

Example 7 was designed to illustrate the influence of acids and salts in the bioreactor on the taste of MCYP. The process of Examples 1–5 was followed with the following exceptions. In case A, aqua-ammonia, phosphoric acid and hydrochloric acid were used as mentioned earlier. In case B, ammonium sulfate was applied as a nitrogen source; diammonium phosphate as a phosphorus source; and sodium hydroxide to control the bioreactor pH. By combining 60 gal yeast cream with 60 gal concentrated centrate and pH adjustment with a sodium hydroxide solution, the following composition of MCYP was obtained (percentage basis unless otherwise noted):

| COMPONENTS | MCYP - A | MCYP - B |
|---|---|---|
| Moisture | 5.0 | 3.0 |
| Protein | 37.7 | 34.6 |
| Fat | 4.2 | 3.7 |
| Ash | 26.2 | 24.4 |

13
-continued

| COMPONENTS | MCYP - A | MCYP - B |
| --- | --- | --- |
| Phosphorus | 5.2 | 1.4 |
| Sulfur | 0.2 | 4.2 |
| Chloride | 5.5 | 1.1 |
| Potassium | 3.4 | 4.2 |
| Sodium | 1.5 | 5.4 |
| Calcium | 0.5 | 0.7 |
| Magnesium | 0.2 | 0.2 |
| pH (10% sol) | 4.6 | 4.9 |

The MCYP (Case B), which was produced with less expensive and more common ingredients, resulted in a chemical/salty off-taste while the product of Case A had a pleasant, acid/salty taste.

Example 8

Example 8 was designed to illustrate the difference between reverse osmosis and evaporation. Following the procedure of Examples 1–5, the evaporation step, which normally results in a centrate effluent having a BOD value below 20 ppm, was replaced by reverse osmosis. The composition of the centrate, which was fed to a lab reverse osmosis unit (plate-and-frame type, membrane Filmtec-HR98), was as follows: 0.7% T.S., pH 3.8, residual yeast cells 6%, residual carbohydrates 0.6 g/l and BOD value of 1500 ppm. The pressure applied in the reverse osmosis process was 40 bar. The centrate was concentrated 12X and had 5.9% T.S. The centrate effluent had a BOD value of 83 ppm, and the average permeate flux was 27.5 $l/m^2h$ during a 1.5 hour run.

Industrial conditions were simulated in a 3-stage reverse osmosis installation (spiral-wound system) provided with 39 $m^2$ Filmtec HR98 membranes. The two types of centrate used for the test runs were disposed at two levels of separation efficiency namely 86% (case A) and 99% (case B). Both centrates had a pH of 3.8 and a residual carbohydrate level of 0.15 g/l. Centrate A contained 0.46% T.S. and centrate B contained 0.32% T.S., due primarily to differences in separation efficiency. The centrates were concentrated to a high rate at a temperature of 108° F. (42° C.) and a pressure of 40 bar. In both cases, the running time was 22 hr. In case A, the centrate was concentrated to 17X and the final concentrated centrate contained 7.7% T.S.; the permeate flux was 6 $l/m^2h$ and the centrate effluent had a BOD value of 95 ppm. In case B, the centrate was concentrated further to 19X and the concentrated centrate contained 6.3% T.S.; the permeate flux was 9 $l/m^2h$ and the BOD value of the centrate permeate was 57 ppm.

Example 9

Example 9 was designed to illustrate the effect of autolysis on the present invention. According to the procedures mentioned in Examples 1–5, a mixture of concentrated centrate (60 gal) and yeast cream (60 gal) was autolyzed. The original centrate had a residual carbohydrate level of 0.4 g/l. The autolysis process was carried out at a pH of 4.5 and a temperature of 122° F. (50° C.) during a 21 hr. period. A part of the protein was broken down during autolysis. The non-protein nitrogen (NPN) fraction on a total protein basis was increased from 40% (Examples 1 and 2) to 56% (Examples 3 and 4). After autolysis the mixture was divided into two parts. The mixture in Example 3 was kept at the original pH of 4.5, while the pH of Example 4 was increased by a sodium hydroxide solution to pH 6.0. Both examples were subsequently inactivated and drum dried. Powder from Example 3 had a sour, bouillon taste and a sodium content of 1.4%, while the powder of Example 4 had a saltier, bouillon taste and 2.7% sodium. The tasting was carried out in a 2% solution at a temperature of 120° F. (50° C.). Both autolyzed powders were used for pet food and compared with their non-autolyzed counterparts.

The dog food was prepared from a mixture of cereals, meat and animal by-products; a mixture of oil and fat; fish and fish byproducts; and yeast and minerals. Its chemical composition was the following: 25% protein, 10% fat, 6.5% ash, 3% fiber and 10% moisture. The cereals were extruded, and the ingredients were pelletized.

The autolyzed and the non-autolyzed products of Examples 2 and 4 were sprayed onto the dog food at a concentration of 1% (w/w). Both products were tested by a group of eight dogs over a period of three days (Department of Animal Nutrition-University of Gent-Belgium). Five of the eight dogs preferred the feed in which the autolyzed product was used. It was concluded that autolysis had a favorable effect on the palatability of dog food.

The cat food was prepared from a mixture of cereals; meat and animal byproducts; a mixture of oil and fat; plant protein digests; fish and fish byproducts; minerals; vitamins and brewers yeast. Its chemical composition was the following: 32% protein, 13% fat, 6.5% ash, 2.5% fiber and 10% moisture. The cereals were extruded and the ingredients were pelletized (control). The autolyzed and non-autolyzed powders (Examples 1 and 3) were sprayed onto the control in a concentration of 2%. Again, a group of eight animals were used during a three-day period. Six of the eight cats preferred the feed in which the autolyzed product was incorporated. It was concluded that autolysis had a favorable effect on palatability. Thereafter, the autolyzed powder from Example 3 was sprayed-onto the control and compared to the control itself. Seven of the eight cats preferred the pet food enriched with the autolyzed powder from Example 3.

Examples 10–16

Examples 10–16 illustrate the process of Examples 1–5 with the substitution of *K. marxianus* for *C. intermedia*. These examples also illustrate the effect of external enzymes on the process and the difference between adding the concentrated centrate before or after autolysis.

Following the procedure in Examples 1–5, *C. intermedia* was replaced by *K. marxianus*. The culture conditions were slightly altered by increasing the temperature to 108° F. (42° C.) and by avoiding oxygen limiting conditions. The residual carbohydrate level after the bioreactor was 0.2 g/l. Pancreatin, an external proteolytic enzyme, was incorporated into the autolysis process of examples. Pancreatin was added in an amount of 0.8% based on the yeast cream solids. The pH was adjusted by a sodium hydroxide solution to 6. The hydrolysis was carried out at 122° F. (50° C.) over a period of 4 hrs., after which inactivation and drum drying were applied. In Example 13, hydrolysis took place on the yeast cream (60 gal) only; the concentrated centrate (60 gal) was added after the hydrolysis step was completed. In Example 14, the hydrolysis was carried out using an earlier mentioned procedure (mixture of concentrated centrate and yeast cream). For Examples 13 and 14, the non-protein nitrogen fraction based on total protein was 56 and 76%, respectively. The taste of a 2% solution (120° F.) of Example 13 was judged to be slightly cheesy, while Example 14 had a stronger cheese flavor.

The proteolytic enzyme papain was then incorporated into the mixture of concentrated centrate and yeast cream. Before autolysis the pH of the mixture was adjusted to 6 with a sodium carbonate solution. Papain was added to the cream solids in an amount of 0.35% (w/w) and hydrolysis took place at 127° F. (53° C.) during a two-hour period, after which inactivation and drum drying were carried out (Example 16). The non-protein nitrogen fraction was 68% this time while the glutamic acid content of the powder was 0.9%. The taste was characterized as a strong bouillon flavor. The hydrolyzed product was applied in an instant cream mushroom soup having the following formula:

|  | grams |
|---|---|
| a fat concentrate based on milk protein | 4.0 |
| potato starch | 4.3 |
| maltodextrin | 6.1 |
| salt | 1.2 |
| hydrolyzed MCYP (Example 16) | 1.0 |
| onion powder | 0.1 |
| white pepper | 0.01 |
| laurel powder | 0.01 |
| freeze-dried mushrooms | 0.20 |
| freeze-dried chives | 0.05 |
| Total | 16.97 |
| boiling water | 180.0 |

The premix of all dry ingredients was mixed with boiling water and stirred for a few minutes. The mushroom soup had a well-balanced taste without the usually high levels of glutamic acid.

Examples 10–12

Autolysis/Hydrolysis of the Yeast *Kluyveromyces marxianus* Under Various Circumstances Followed by Drum Drying

| Examples | 10 | 11 | 12 |
|---|---|---|---|
| Batch No. | T36 | T38 | T39 |
| Conditions | cream[1] | mixture[1] | cream[2] |
|  | pH 4.5 | pH 4.5 | pH 6 |
|  | 21 h | 21 h | 4 h |
|  | 122° F. | 122° F. | 122° F. |
|  |  |  | H (0.8%)[3] |
| Protein breakdown |  |  |  |
| NPN/TN (%) | 48 | 52 | 62 |
| Free glutamic acid (%) | 2.1 | 0.9 | 2.7 |
| Taste (2% sol.) | bad bouillon | very sour yeasty | flat cheesy |
| Color[4] | + | + | +/− |
| Res. Carboh. (g/l) | 0.15 | 0.15 | 0.15 |
| Composition |  |  |  |
| protein | 45 | 43 | 44 |
| fat | 4 | 4 | 5 |
| ash | 9 | 17 | 8 |
| Ash composition |  |  |  |
| phosphorus | 2.0 | 5.2 | 2.1 |
| chloride | 0.6 | 1.8 | 0.3 |
| sulfur | 0.2 | 0.2 | 0.3 |
| potassium | 2.3 | 4.3 | 2.6 |
| sodium | 0.3 | 1.3 | 0.8 |
| calcium | 0.1 | 0.8 | 0.1 |
| magnesium | 0.2 | 0.2 | 0.2 |
| pH (10% sol.) | 4.5 | 4.4 | 6.1 |

[1]autolysis conditions
[2]hydrolysis (H) conditions
[3]hydrolysis with 0.8% pancreatin; enzyme dosage calculated on yeast cream solids
[4]− = white/yellow; + = tan Examples 13–14

Hydrolysis of the Yeast *Kluyveromyces marxianus* Under Various Circumstances Followed by Drum Drying

| Examples | 13 | 14 |
|---|---|---|
|  | T40 | T41 |
| Conditions | cream[1] | mixture[1] |
|  | pH 6 | pH 6 |
|  | 4 h | 4 h |
|  | 122° F.[2] | 122° F.[2] |
|  | after H con. centr. |  |
| Protein breakdown |  |  |
| NPN/TN (%) | 56 | 76 |
| Free glutamic acid (%) | 1.0 | 1.3 |
| Taste (2% sol.) | salty cheese | strong cheese |
| Color[3] | + | ++ |
| Res. Carboh. (g/l) | 0.15 | 0.15 |
| Composition |  |  |
| protein | 40 | 37 |
| fat | 4 | 4 |
| ash | 22 | 27 |
| Ash composition |  |  |
| phosphorus | 4.0 | 4.5 |
| chloride | 1.7 | 2.4 |
| sulfur | 0.2 | 0.2 |
| potassium | 3.4 | 5.6 |
| sodium | 1.4 | 4.7 |
| calcium | 0.7 | 0.9 |
| magnesium | 0.3 | 0.3 |
| pH (10% sol.) | 4.5 | 5.4 |

[1]hydrolysis (H) conditions
[2]hydrolysis with 0.8% pancreatin; enzyme dosage calculated on yeast cream solids
[3]+ = tan; ++ = light brown Examples 15–16

Hydrolysis of the Yeast *Kluyveromyces marxianus* Under Various Circumstances Followed by Drum Drying

| Examples | 15 | 16 |
|---|---|---|
|  | T44 | T45 |
| Conditions | mixture[1] | mixture[1] |
|  | pH 4.5 | pH 6 |
|  | 2 h | 2 h |
|  | 127° F.[2] | 127° F.[2] |
| Protein breakdown |  |  |
| NPN/TN (%) | 65 | 68 |
| Free glutamic acid (%) | 0.7 | 0.9 |
| Taste (2% sol.) | acid bouillon | strong bouillon |
| Color[3] | ++ | ++ |
| Res. Carboh. (g/l) | 0.20 | 0.20 |
| Composition |  |  |
| protein | 40 | 41 |

Hydrolysis of the Yeast *Kluyveromyces marxianus* Under Various Circumstances Followed by Drum Drying

| | | |
|---|---|---|
| fat | 3 | 3 |
| ash | 21 | 21 |
| Ash composition | | |
| phosphorus | 5.3 | 4.4 |
| chloride | 1.8 | 1.8 |
| sulfur | 0.2 | 0.2 |
| potassium | 4.9 | 3.9 |
| sodium | 1.8 | 2.1 |
| calcium | 0.7 | 0.8 |
| magnesium | 0.3 | 0.2 |
| pH (10% sol.) | 4.6 | 4.5 |

[1] hydrolysis conditions
[2] hydrolysis with 0.35% papain; enzyme dosage calculated on yeast cream solids
[3] ++ = light brown

Example 17

In this example, the production of MCYP is combined with the manufacture of lactose instead of inactivated dried yeast. A quantity of 2,300 gal. UF-permeate (5% TS) is acidified to pH 4.5 by phosphoric acid to limit sedimentation during the subsequent lactose manufacturing processes, known to the art. The UF-permeate is concentrated to 50% TS and further processed in crystallization facilities. After removal of the lactose crystals and further purification to the required lactose quality, the product is dried. At a lactose yield of 47%, approximately 400 lbs. of lactose will be obtained. After lactose manufacture, a partially delactosed permeate will remain, which is diluted with potable water to 1,600 gal. This substrate is cultured by means of the yeast *K. marxianus*.

The adjustment of the pH to 3.8 is preferably carried out by hydrochloric acid, and the total amount of the separated yeast cream is combined with all of the concentrated centrate. After autolysis and drying, a total amount of approximately 400 lbs of MCYP with flavor enhancing properties will be obtained.

It is understood that the invention is not confined to the particular construction and arrangement herein illustrated and described, but embraced such modified forms thereof as come within the scope of the following claims.

What is claimed is:

1. A process for producing a modified cultured yeast product from a whey permeate comprising:
   a. heat treating a whey permeate at a temperature between about 162° F. (72° C.) and 185° F. (85° C.) for a time sufficient to inactivate undesirable microorganisms in the permeate;
   b. inoculating the heat-treated whey permeate with a yeast culture in a bioreactor and maintaining the inoculated whey permeate in the bioreactor under yeast growth conditions until a yeast product is produced in the whey permeate, wherein the yeast culture is selected from the group consisting of *Kluveromyces marxianus* and *Candida intermedia*;
   c. separating the yeast product into a yeast cream and a yeast centrate;
   d. combining the yeast cream and the yeast centrate in quantities such that the ratio of total solids of the yeast cream to the total solids of the yeast centrate is between approximately 0.3 and 1.6;
   e. autolyzing the combination of step d. under sufficient conditions to produce an edible modified yeast product; and
   f. heating the yeast product under sufficient conditions to inactivate undesirable microorganisms to produce the modified cultured yeast product.

2. The process of claim 1 wherein the yeast cream has a total solids level between about 10 and 30% (w/v).

3. The process of claim 1 wherein the centrate has a total solids level between about 5 and 40% (w/v).

4. The process of claim 1 wherein the modified cultured yeast product is hydrolyzed following step e.

5. The process of claim 1 wherein the modified cultured yeast product is subsequently dried.

* * * * *